United States Patent [19]
Arndt et al.

[11] 4,294,605
[45] Oct. 13, 1981

[54] AGENTS FOR THE DEFOLIATION OF PLANTS

[75] Inventors: Friedrich Arndt; Reinhard Rusch; Heinz Schulz, all of Berlin, Fed. Rep. of Germany

[73] Assignee: Schering Aktiengesellschaft, Berlin and Bergkamen, Fed. Rep. of Germany

[21] Appl. No.: 96,577

[22] Filed: Nov. 21, 1979

Related U.S. Application Data

[63] Continuation of Ser. No. 651,522, Jan. 22, 1976, abandoned.

[30] Foreign Application Priority Data

Feb. 14, 1975 [DE] Fed. Rep. of Germany ....... 2506690

[51] Int. Cl.$^3$ ............................................. A01N 43/82
[52] U.S. Cl. ............................................. 71/73; 71/90
[58] Field of Search ...................................... 71/73, 90

[56] References Cited

U.S. PATENT DOCUMENTS

| | | | |
|---|---|---|---|
| 3,734,923 | 5/1973 | Dowding et al. | 71/90 X |
| 3,827,875 | 8/1974 | Krenzer | 71/90 |
| 3,874,874 | 4/1975 | Cebalo et al. | 71/90 |
| 3,883,547 | 5/1975 | Schulz et al. | 71/90 X |

*Primary Examiner*—Catherine L. Mills
*Attorney, Agent, or Firm*—Michael J. Striker

[57] ABSTRACT

The invention concerns an agent for defoliating plants and which contains as active substance 1,2,3-thiadiazolyl ureas.

3 Claims, No Drawings

AGENTS FOR THE DEFOLIATION OF PLANTS

This is a continuation, of application Ser. No. 651,522, filed Jan. 22, 1976, now abandoned.

In the normal life process of a plurality of plant types, due to environmental conditions or certain processes within a plant, a group of special cells, e.g. at the base of the leaf stalk, is altered to meristematic cells. They form a dividing layer, so that in the end the leaves drop off. This, however, often does not take place at the desired time or to the desired extent; one tries, therefore, to achieve this process in a controlled manner at a certain time or stage of development of the plants.

Such a controlled defoliation is of special economic importance because of the easier harvesting and accelerated ripening obtainable thereby in agricultural and horticultural crops or also as indirect measures of controlling insects, fungi or bacteria injurious to plants.

For this purpose, aliphatic thiophosphates, particularly tri-n-butyl-trithiophosphate, have been proposed before according to U.S. Pat. No. 2,965,467. This active substance, however, has not always a satisfactory effect, and, furthermore, affects in many instances persons handling it because of its unpleasant odor.

It has now been found that an agent containing a compound of the general formula

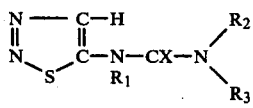 I.

in which $R_1$ is hydrogen or a low alkyl, $R_2$ is hydrogen or an alkyl possibly substituted or interrupted once or several times by oxygen or sulfur atoms, $R_3$ is alkyl possibly substituted or interrupted once or several times by oxygen or sulfur atoms, a cycloaliphatic hydrocarbon radical possibly substituted once or several times by alkyl, or an aromatic hydrocarbon radical substituted once or several times by alkyl and/or halogen and/or alkyl mercapto and/or alkoxy and/or trifluoromethyl and/or the nitrogen group, or $R_2$ and $R_3$ together with the N atom, the morpholino, piperidino, or pyrrolidino group, or X is an oxygen or sulfur atom, is distinctly superior to the known agent in the effect and avoids the disadvantages thereof.

As active substances of the stated general formula, those compounds in which the radical $R_1$ is hydrogen or alkyl with 1 to 3 carbon atoms, such as methyl or ethyl, the radical $R_2$ is hydrogen or alkyl with 1 to 4 carbon atoms, such as methyl or ethyl, the radical $R_3$ is alkyl with 1 to 4 carbon atoms, such as methyl or ethyl, cycloalkyl with 5 to 8 carbon atoms, such as cyclopentyl, cyclohexyl or methylcyclohexyl, or a phenyl, halphenyl, methylphenyl or methoxyphenyl radical, and X is oxygen or sulfur, are particularly suitable.

With respect to its defoliating effect, the agent of the invention is greatly effective and can be used, for example, in tree nurseries, fruit and vegetable cultivations, legumes, grape vines, roses, and in particular cotton. The plants or plant parts to be harvested are thereby made both more easily accessible in an advantageous manner and also accelerated considerably in their ripening. Under proper environmental conditions, plants thus treated later form again sound normal foliage.

While the crop plants named as an example shed foliage only under specific physiological conditions or under special environmental conditions; malvaceae react extremely sensitively and drop their foliage leaves after a treatment with the characterized agent, being much less dependent on special conditions.

The agents to be used according to the invention are suitable particularly for defoliating cotton plants, making it possible to an extent not previously attained to use picking machines for the capsule harvest.

The quantities applied for the desired defoliation are 1-10,000 g active substance per hectare.

The compounds to be used according to the invention can be used either alone, in mixture with one another or with other active substances. Optionally other defoliants, plant protectants or pest control agents may be added according to the desired purpose.

Promotion of the action and of the velocity of action can be achieved, for example, by action-increasing additions, such as organic solvents, wetting agents and oils. This permits a reduction of the quantity of use of the actual active substance.

Advantageously the characterized active substances or their mixtures are used in different preparations, such as powders, scatters, granulations, solutions, emulsions or suspensions, with addition of liquid and/or solid vehicles or diluents and optionally of wetting, adhesive, emulsifying and/or dispersing aids.

Suitable liquid vehicles that may be used are, for example, water, aliphatic and aromatic hydrocarbons, such as benzene, toluene, xylene, cyclohexanone, isophorone, dimethyl sulfoxide, dimethyl formamide, also mineral oil fractions.

As solid vehicles that may be used are suitable mineral earths like siliceous clay, silica gel, talc, kaolin, attaclay, limestone, silica, and plant products, such as flours.

Among the surface active substances that may be used are calcium-lignin sulfonate, polyoxyethyleneoctylphenol ether, naphthalene sulfonic acids and their salts, phenolsulfonic acids and their salts, formaldehyde condensates, fatty alcohol sulfates as well as substituted benzenesulfonic acids and their salts.

The proportion of active substance(s) in the various preparations may vary within wide limits. For example, the agents contain about 10 to 80 weight percent of active substances, about 90 to 20 weight percent of liquid or solid vehicles and optionally up to 20 weight percent of surface-active substances.

The application of the agents can be carried out in the usual manner, e.g. with water as vehicle in spray solution quantities of about 100 to 1000 liters per hectare. Use of the agents in the so-called "Low Volume" and "Ultra Low Volume Process" is also possible, as is their application in the form of so-called micro granulates.

The compounds to be used according to the invention are known and can be produced by usually known methods, such as by the reaction of the respective amino compounds with carbamoyl halides, chloroformic acid esters or isocyanates or with phosgene and the subsequent reaction of the isocyanate or carbamoyl halide with a corresponding amine to the desired process products. The thio compounds are prepared using the analogous sulfur-containing starting compound.

The manufacture of these products occurs, therefore, for example, by reacting compounds of the general formula

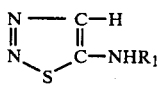   II.

(a) with carbamoyl or thiocarbamoyl chlorides of the general formula

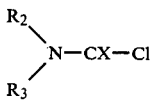   III.

in the presence of an acid acceptor, expediently an inorganic or tertiary organic base, such as sodium carbonate or triethylamine, or (b) with chloroformic acid esters or chlorothioformic acid esters of the general formula $$Cl-CX-O-R_4 \qquad \text{IV.}$$

in the presence of an acid acceptor, such as triethylamine, then causing reaction with amines of the general formula

   V.

or (c) first exposing them to phosgene or thiophosgene in the presence of an acid acceptor, such as N,N-dimethyl aniline, with formation of the respective isocyanate or carbamoyl chloride, and then reacting with an amine of the general formula

   VI.

or, (d) if $R_2$ signifies hydrogen, exposing them to isocyanate or isothionates of the general formula $$R_3-N=C=X \qquad \text{VII.}$$

in the presence of a catalyst, preferably an organic base, such as triethylamine, $R_1$, $R_2$, $R_3$ and X having the above meaning, and $R_4$ representing a low alkyl radical, like methyl or ethyl.

The following examples will illustrate the production of the active substances to be used according to the invention.

1. N-phenyl-N'-1,2,3-thiadiazole-5-yl Urea

Combine 10.1 g (0.1 mole) 5-amino-1,2,3-thiadiazole, 75 ml of tetrahydrofurane and 11.5 ml (0.106 mole) of phenyl isocyanate. Further add 0.1 ml of triethylamine as catalyst. After standing overnight, the first crystals will have precipitated. The solvent is removed by evaporation under vacuum, and the residue is recrystallized from isopropanol.

M.p.: 217° C. (decomposition).
Yield: 16.9 g = 76.7% of the theory.

2. N-ethyl-N-phenyl-N'-(1,2,3-thiadiazole-5-yl) Urea

Dissolve 11.05 g (0.05 mole) of the 5-phenoxycarbonylamino-1,2,3-thiadiazole produced in the usual manner from 5-amino-1,2,3-thiadiazole and chloroformic acid phenyl ester in 100 ml of N,N-dimethyl formamide and admix with 12.6 g (0.1 mole) of N-ethyl aniline. Maintain the mixture at a temperature of 90° to 100° C. for 6 hours while stirring. After the reaction mixture has cooled, dilute with water, whereby the urea precipitates as a light brown deposit. The product is suctioned off, washed with benzene and dried. One obtains 10.2 g (82.1% of the theory) of pure urea of the melting point 200° C.

M.p.: 200° C. (decomposition).
Yield: 10.2 g = 82.1% of the theory.

In an analogous manner the following active substances can be produced. Note: In the table D means decomposition.

| | Active Substance | Physical Constant |
|---|---|---|
| 3. | N-(4-chlorophenyl)-N'-(1,2,3-thiadiazole-5-yl) urea | M.p.: 256° C. (D) |
| 4. | N-cyclohexyl-N'-1,2,3-thiadiazole-5-yl urea | M.P.: 215° C. (D) |
| 5. | N-(chlorophenyl)-N'-(1,2,3-thiadiazole-5-yl) urea | M.P.: 244° C. (D) |
| 6. | N-(4-methylphenyl)-N'-(1,2,3-thiadiazole-5-yl) urea | M.P.: 228° C. (D) |
| 7. | N-(3-methylphenyl)-N'-(1,2,3-thiadiazole-5-yl) urea | M.P.: 208° C. (D) |
| 8. | N-(3,4-dichlorophenyl)-N'-(1,2,3-thiadiazole-5-yl) urea | M.P.: 236° C. (D) |
| 9. | N-methyl-N'-(1,2,3-thiadiazole-5-yl) urea | M.P.: 174° C. |
| 10. | N,N-dimethyl-N'-(1,2,3-thiadiazole-5-yl) urea | M.P.: 222° C. (D) |
| 11. | N,N-dimethyl-N'-methyl-N'-(1,2,3-thiadiazole-5-yl) urea | M.P.: 129° C. |
| 12. | N-methyl-N'-methyl-N'-(1,2,3-thiadiazole-5-yl) urea | M.P.: 221° C. |
| 13. | N-phenyl-N'-(1,2,3-thiadiazole-5-yl) thiourea | M.P.: 205°C. (D) |
| 14. | N-(4-chlorophenyl)-N'-(1,2,3-thiadiazole-5-yl) thiourea | M.P.: 213° C. (D) |
| 15. | N-methyl-N-phenyl-N'-(1,2,3-thiadiazole-5-yl) urea | M.P.: 184° C. (D) |
| 16. | N-ethyl-N-phenyl-N'-(1,2,3-thiadiazole-5-yl) urea | M.P.: 200° C. (D) |
| 17. | N-propyl-N-phenyl-N'-(1,2,3-thiadiazole-5-yl) urea | M.P.: 190° C. (D) |
| 18. | N-butyl-N-phenyl-N'-(1,2,3-thiadiazole-5-yl) urea | M.P.: 198° C. (D) |
| 19. | N-(2-chlorophenyl)-N'-(1,2,3-thiadiazole-5-yl) urea | M.P.: 237° C. (D) |
| 20. | N-(2-methylphenyl)-N'-(1,2,3-thiadiazole-5-yl) urea | M.P.: 197° C. (D) |
| 21. | N-(2-nitrophenyl)-N'-(1,2,3-thiadiazole-5-yl) urea | M.P.: 229° C. (D) |
| 22. | N-(3-nitrophenyl)-N'-(1,2,3-thiadiazolyl-5-urea | M.P.: 252° C. (D) |
| 23. | N-methyl-N-(2-methylphenyl)-N'-(1,2,3-thiadiazole-5-yl) urea | M.P.: 215° C. (D) |

The above compounds are crystalline substances which are very slightly soluble in aliphatic and aromatic hydrocarbons and in water and are well soluble in polar organic solvents, such as acetone, cyclohexanone, isophorone, dimethyl sulfoxide and dimethyl formamide, depending on the respective substitution.

The starting products for the manufacture of the compounds according to the invention are known in themselves or can be produced by known methods.

Some of the compounds to be used according to the invention have already been proposed as agents for control of plant growth. The agents exert an inhibiting action, resulting in a delay of the vegetative growth (DT-OS No. 2,214,632).

The discovery of the effect of these compounds influencing the leaf shedding of plants was surprising especially because this effect was in drastic contrast to the known delaying effect and, therefore, was even less to be expected.

The following examples will serve to illustrate the invention.

EXAMPLE 1

Potted seedlings of cotton were treated in the stage of 5–6 developed true foliage leaves. The quantities of the compound of the invention and of the comparison agents applied in 500 liters of water per hectare can be seen in the table.

Two weeks after the treatment, the number of foliage leaves still present was determined. The results are listed as percentual defoliation as compared with the number of foliage leaves present before the treatment.

|   | Active substance | kg active subst. ha | Defoliation in % |
|---|---|---|---|
| 1. | N-phenyl-N'-1,2,3-thiadiazole-5-yl urea | 0.5 | 94.4 |
|   | Comparison agents | | |
| 2. | Tri-n-butyl-trithiophosphate | 0.7 | 38.9 |
| 3. | Sodium chloride | 1 | 0 |
| 4. | Untreated | 0 | 0 |

Analogous effects could be obtained also with the following active substances.

Active substances

5. N-(4-chlorophenyl)-N'-1,2,3-thiadiazole-5-yl urea
6. N-cyclohexyl-N'-1,2,3-thiadiazole-5-yl urea
7. N-(3-chlorophenyl)-N'-1,2,3-thiadiazole-5-yl urea
8. N-(4-methylphenyl)-N'-1,2,3thiadiazole-5-yl urea
9. N-(3-methylphenyl)-N'-1,2,3-thiadiazole-5-yl urea
10. N-(3,4-dichlorophenyl)-N'-1,2,3-thiadiazole-5-yl urea
11. N-methyl-N'-1,2,3-thiadiazole-5-yl urea
12. N,N-dimethyl-N'-1,2,3-thiadiazole-5-yl urea
13. N,N-dimethyl-N'-methyl-N'-1,2,3-thiadiazole-5-yl urea
14. N-methyl-N'-methyl-N'-1,2,3-thiadiazole-5-yl urea
15. N-phenyl-N'-1,2,3-thiadiazole-5-yl thiourea
16. N-(4-chlorophenyl)-N'-1,2,3-thiadiazole-5-yl thiourea
17. N-methyl-N-phenyl-N'(1,2,3-thiadiazole-5-yl) urea
18. N-ethyl-N-phenyl-N'-(1,2,3-thiadiazole-5-yl) urea
19. N-propyl-N-phenyl-N'-(1,2,3-thiadiazole-5-yl) urea
20. N-butyl-N-phenyl-N'-(1,2,3-thiadiazole-5-yl) urea
21. N-(2-chlorophenyl)-N'-(1,2,3-thiadiazole-5-yl) urea
22. N-(2-methylphenyl)-N'-(1,2,3thiadiazole-5-yl) urea
23. N-(2-nitrophenyl)-N'-(1,2,3-thiadiazole-5-yl) urea
24. N-(3-nitrophenyl)-N'-(1,2,3-thiadiazolyl-5-yl) urea
25. N-methyl-N-(2-methylphenyl)-N'-(1,2,3-thiadiazole-5-yl) urea

EXAMPLE 2

Potted cotton plants were treated in the stage of beginning flower bud formation as indicated in Example 1.

The results are listed in the following table.

|   | Active substance | kg active subst,/ha | Defoliation in % |
|---|---|---|---|
| 1. | N-phenyl-N'-1,2,3-thiadiazole-5-yl urea | 0.5 | 91.0 |
| 2. | N-phenyl-N'-1,2,3-thiadiazole-5-yl thiourea | 0.5 | 90.4 |
| 3. | 1-(2-methylphenyl)-3-(1,2,3-thiadiazole-5-yl) urea | 0.5 | 87.1 |
| 4. | 1-methyl-1-phenyl-3-(1,2,3-thiadiazole-5-yl) urea | 0.5 | 92.3 |
|   | Comparison agent | | |
| 5. | Tri-n-butyl-trithiophosphate | 0.7 | 72.0 |
| 6. | Untreated | 0 | 0 |

EXAMPLE 3

Cotton plants were treated as in Example 1 in the stage of bud formation.

Some of the aqueous suspensions contained as a further additive dimethyl sulfoxide in the stated concentration. The results in the following table confirm an increase in action achieved by addition of dimethyl sulfoxide.

|   | kg/ha I | II | Defoliation in % |
|---|---|---|---|
| N-Phenyl-N'-1,2,3-thiadiazole-5-yl urea (I) | 0.05 | | 81.8 |
| Dimethyl sulfoxide (II) | | 15.0 | 0 |
| I + II | 0.05 | 0.15 | 83.7 |
| I + II | 0.05 | 15.0 | 95.6 |

EXAMPLE 4

Cotton plants were treated as in Example 1 in the stage of ripeness of the capsules. The aqueous suspensions contained as further additives a non-phytotoxic paraffin oil partly in combination with dimethyl sulfoxide in the stated concentrations.

The results can be seen from the following table and show an increase of the defoliation caused by the additive.

|   |   | kg/ha I | II | III | Defoliation in % |
|---|---|---|---|---|---|
| 1. | N-phenyl-N'-1,2,3-thiadiazole-5-yl-ureas(I) | 0.05 | | | 45.4 |
| 2. | Paraffin oil (II) | | 5.0 | | 0 |
| 3. | Dimethyl sulfoxide (III) | | | 5.0 | 0 |
|   | I + II | 0.05 | 0.5 | | 61.8 |
|   | I + II + III | 0.05 | 2.5 | 2.5 | 94.1 |

EXAMPLE 5

In a field test, apple trees (Cox Orange Renette) were sprayed two weeks after their bloom with a 0.03% and a 0.009% aqueous suspension of N-phenyl-N'-1,2,3thiadiazole-5-yl urea. This led to shedding of the leaves on the young long shoots, which, however, were not influenced in their further growth.

EXAMPLE 6

Young plants of Hibiscus rosa-sinensis were sprayed with an aqueous suspension of N-phenyl-N'-1,2,3-thiadiazole-5-yl urea in quantities for a rate of 0.005 kg/ha, 0.05 kg/ha and 0.5 kg/ha. Regardless of the doses of active substance applied here, the foliage had been shed completely a few days after the treatment. 1-Butyl-1-phenyl-3-(1,2,3-thiadiazole-5-yl) urea achieved a similar effect, while tri-n-butyltrithiophosphate caused no defoliation either with 0.05 or with 0.5 kg active substance per hectare.

EXAMPLE 7

| Production of a spray powder | |
|---|---|
| 50.0 percent by weight | N-phenyl-N'-1,2,3-thiadiazole-5-yl urea as active substance |
| 1.0 percent by weight | Wetting agent on sodium alkyl-naphthalene sulfonate base |
| 20.0 percent by weight | Surface-active substance on calcium lignin sulfonate base |
| 29.0 percent by weight | Aluminum silicate as vehicle |

The components were ground in a pin mill to a finely dispersed powder and resulted in the agent ready to use, which can be diluted with water to the desired suspension.

EXAMPLE 8

| Production of an active substance solution | |
|---|---|
| 20.0 percent by weight | N-phenyl-N'-1,2,3-thiadiazole-5-yl urea |
| 40.0 percent by weight | Dimethyl sulfoxide |
| 40.0 percent by weight | Xylene |

The active substance is mixed with the other components while stirring and results in a solution ready for use and which can be applied in so-called Ultra-Low-Volume, such as when using aircraft.

After admixing surface-active agents, such as emulsifiers, so-called emulsion concentrates form, which can be used after dilution with water.

We claim:

1. Method for defoliating cotton plants, comprising applying to the plants N-phenyl-N$^1$-1,2,3-thiadiazol-5-yl urea of the formula

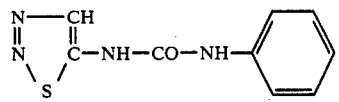

in mixture with liquid or solid carriers.

2. Method according to claim 1, wherein said mixture additionally contains adjuvants selected from the group consisting of dimethyl sulfoxide and non-phytotoxic paraffin oil.

3. Method according to claim 2, wherein said mixture contains 1 to 300 parts by weight of said additions per 1 part by weight of said N-phenyl-N$^1$-1,2,3-thiadiazol-5-yl urea.

* * * * *